United States Patent
Chen

(10) Patent No.: US 6,518,450 B2
(45) Date of Patent: Feb. 11, 2003

(54) GUAIACOXYPROPANOLAMINES WITH ALPHA/BETA ADRENERGIC BLOCKING ACTIVITY

(75) Inventor: Ing-Jun Chen, Kaohsiung (TW)

(73) Assignee: National Science Council, Taipei (TW)

( * ) Notice: Subject to any disclaimer, the term of this patent is extended or adjusted under 35 U.S.C. 154(b) by 0 days.

(21) Appl. No.: 09/740,754

(22) Filed: Dec. 20, 2000

(65) Prior Publication Data

US 2001/0056211 A1 Dec. 27, 2001

Related U.S. Application Data

(63) Continuation of application No. 09/126,881, filed on Jul. 30, 1998, now abandoned.

(30) Foreign Application Priority Data

Jul. 31, 1997 (TW) .......................................... 86110917

(51) Int. Cl.[7] ............................................. C07C 229/00
(52) U.S. Cl. ........................... 560/38; 560/37; 562/444; 564/192
(58) Field of Search ...................... 560/37, 38; 562/442, 562/443, 444; 564/192

(56) References Cited

U.S. PATENT DOCUMENTS 3,857,891 A * 12/1974 Holmes et al.
3,934,032 A * 1/1976 Barrett et al.
4,165,384 A * 8/1979 Carlsson et al.

OTHER PUBLICATIONS

CA:131:242972 abs of JP11255719 Aug. 1999.*
CA: 132:137174 abs of WO2000005193 Feb. 2000.*

* cited by examiner

Primary Examiner—Jean F. Vollano
(74) Attorney, Agent, or Firm—Chi Ping Chang; Pacific Law Group LLP

(57) ABSTRACT

The present invention reveals a novel structure of guaiacoxypropanolamines shown in formula I:

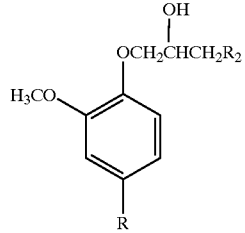

where R is

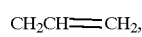

$CH_2CH{=\!=}CH_2$, $CH{=\!=}CHCOOC_2H_3$, $CH{=\!=}CHCH_3$ $CH_2NHCO(CH_2)_7CH_3$-

$R_2$ is

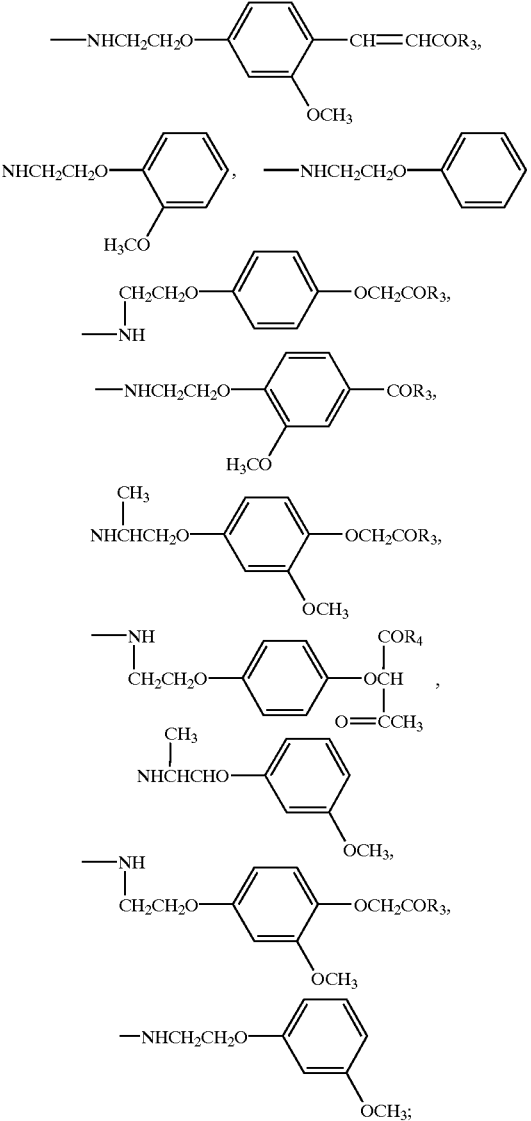

$R_3$ is

OH, $OCH_3$, $NHCH_2CH_2OCH_3$, $CH_2R_6$;

$R_4$ is $OCH_3$, $OC_2H_5$, $CH_2R_6$;

$R_6$ is $C_1$–$C_6$ Saturated Alkyl, $C_1$–$C_6$ Unsaturated Alkyl.

The composition comprising formula I acts as active intergant and pharmaceutical acceptable vehicle. The composition by perfect administration routes in the mammal when given potential α/β-adrenergic blocking, is selective for emergency hypertension.

12 Claims, 1 Drawing Sheet

GUAIACOXYPROPANOLAMINES WITH ALPHA/BETA ADRENERGIC BLOCKING ACTIVITY

This is a continuation application of application Ser. No. 09/126,881 filed on Jul. 30, 1998, now abandoned, of CHEN ET AL for GUCOXYPROPANOLAMINES WITH $\alpha/\beta_{13}$ADRENERGIC BLOCKING ACTIVITY.

BACKGROUND OF THE INVENTION

1. Field of the Invention

This invention pertains to a compounded, innovative guaiacoxypropanolamine structures, upon laboratory testing on animals, has proven that it pharmacologically possesses $\alpha/\beta$-adrenergic blocking activity.

2. Background of the Invention

Adrenergic stimulant β blocker has been in use for 26 years in clinical application; currently, β-adrenergic blocker is not only used in cardiovascular diseases such as high blood pressure, angina-pectoris and cardiac arrhythmia, it is also used in symptoms of thyroid disorders, cardiomegalia, myocardial infarction, migraine, glaucoma, and gastric ulcer. In fact, it has a wide range of application. Yet traditional β blocker still has some unavoidable side-effects, such as it suppresses the cardiovascular function, increases the surrounding and artery vascular resistance, and restricts its clinical application. Therefore, where cardiolegalia is caused by coronary artery cramp, it is not suitable to prescribeβblocker for treatment. Recently developed medication that combines α and β blockers has been used in treating some of the coronary vesicular diseases as it reduces the side-effect of traditional β blocker on one hand, and avoids reversal tachycardia caused by β blocker that generates a cardiac enlargement on the other. Typical α/β blockers include labetalol(Trandate®), which is often used on patients suffering from emergency hypertension.

3. Prior Techniques

In terms of exploring chemical structure and structural activity relationship(SAR) which indicate that the structure of coxyethylamine has a blocking activity, there have been Augestein al et. in 1964, while Kierstead, R. W. al. et. have published in *J. Med. Chem.*, Vol. 26, pp. 1561–69, 1983 that aryloxypropanolamine is the basic structure of β blocker. In addition, many ingredients found in Chinese traditional herbs also contain aryl groups, thus it inspires the interest in locating the composition that contains aryl, which include eugenol, isoeugenol, ferulic acid, capsaicin, and by using chemical reaction to infuse propanol-amine first, and then infusing the structure of guaiacolethylamine to enable the αblocking activity, compounds such as eugenodilol, isoeugendilol, ferulidilol, capsinodilol are obtained. It is then further explored whether the compounded chemicals possess α, β blocking activities, while examining their pharmaceutical properties.

SUMMARY OF THE INVENTION

The primary objective of this invention is to disclose a novel guaiacolethylamine structure as shown in formula I, and its compounding method.

One other objective of this invention is to utilize maximal experiment to verify that Formula I compound does possess α/β guaiacolethylamine blocking activity.

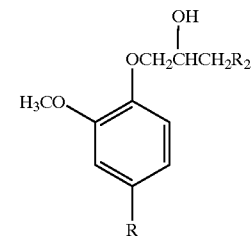

where R is

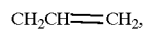

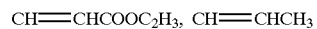

$R_2$ is

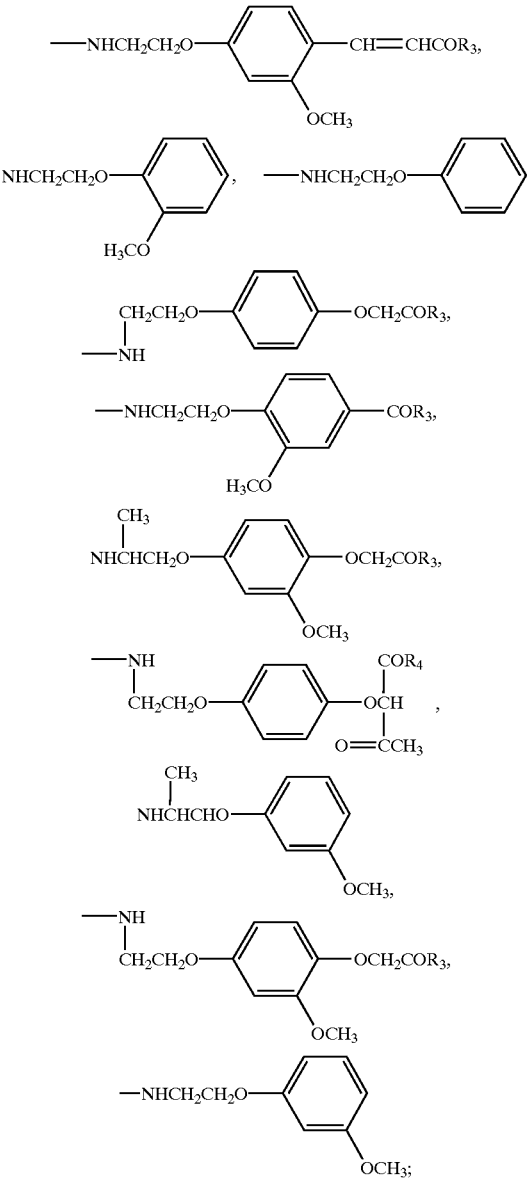

$R_3$ is

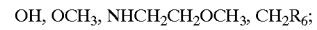

-continued

R$_4$ is

OCH$_3$, OC$_2$H$_5$, CH$_2$R$_6$;

R$_6$ is

C$_1$–C$_6$ Saturated Alkyl, C$_1$–C$_6$ Unsaturated Alkyl.

This invention has one more objective, which is to take the compound in Formula I as the main ingredient and add various definitives so that the pharmaceutic combinations produced will possess α/β guaiacolethylamine blocking activity.

DETAILED DESCRIPTION OF THE INVENTION

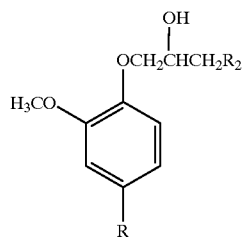

where R is

Figure 1:
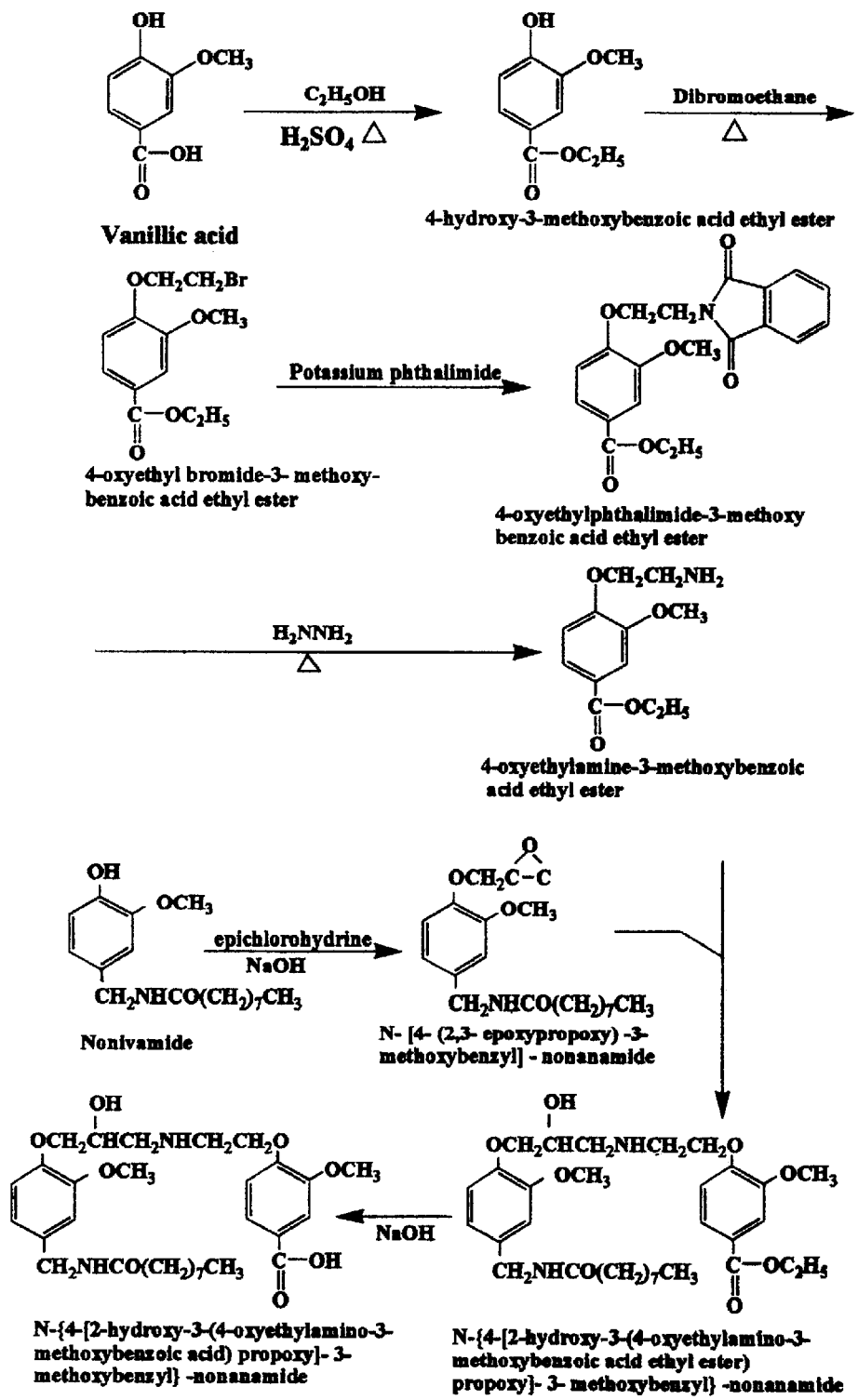
FIG. 1 Compounding methods of the synthetic compounds.

CH$_2$CH=CH$_2$,

CH=CHCOOC$_2$H$_3$, CH=CHCH$_3$

CH$_2$NHCO(CH$_2$)$_7$CH$_3$-

R$_2$ is

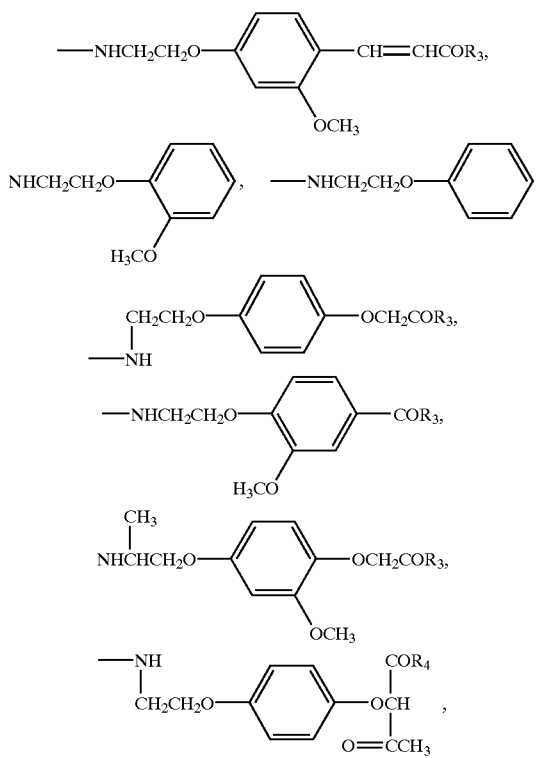

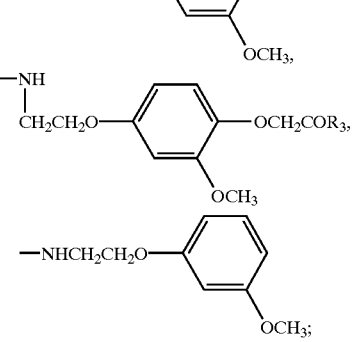

R$_3$ is

OH, OCH$_3$, NHCH$_2$CH$_2$OCH$_3$, CH$_2$R$_6$;

R$_4$ is

OCH$_3$, OC$_2$H$_5$, CH$_2$R$_6$;

R$_6$ is

C$_1$–C$_6$ Saturated Alkyl, C$_1$–C$_6$ Unsaturated Alkyl.

This invention also discloses a novel compounding method for the compound, guaiacolethylamine structure I, as shown in FIG. 1. It comprises of, 1) 4-oxyethylamine-3-methoxybenzoic acid ethyl ester is compounded by placing 4-hydroxy-3-methoxybenzoic acid ethyl ester and ethylene dibromide in a tri-neck flask, heating it to boiling point and stirring in sodium hydroxide. Ethane is mixed with ethyl acid and ethyl ester to form the diluter, and silicone filled tubes are used for separation. After adding equal Molar ratio of potassium phthalimide and the reaction upon heating, an equal Molar ratio of hydrazine hydrate is added to obtain a heating reaction.

2) Compounding epoxide: Under an alkaline condition, elements such as nonivamide, ferulic acid, or 4-hydroxy-3-methoxy-1-propenyl bezene are mixed to obtain a reaction, and epichlorohydrine is then added. Upon fully diffusing, pressurizing and evaporation, and the silicone-filled tubes are separated and white crystallization is obtained.

3) Compounding N-[4-(2-hydroxy-3-(4-oxyethylamino-3-methoxy-benzoic acid)propoxy)-3-methoxy]-1-propylenyl benzene: Take 4-oxyethylamine-3-methoxybenzoic acid ethyl ester and equal Molar ratio of epoxide to obtain an amine reaction and place it overnight for crystallization to form.

For the novel guaiacolethylamine compound above, different substituting bases change its intermediate products. For example, epoxide and (4-oxyethylamine-3-methoxycinnamic acid ethyl ester) may be heated to obtain a reaction. Yet, if ethylene dibromide, ferulic acid, vanillic acid and guaiacol used during the bromine byproduct reactive process are replaced by other dibromides, it may lengthen the byproduct's chain length for 4-oxyethaylamine. When necessary, 3-carbonmethoxy that replaces guaiacol may be esterized to obtain different methoxy byproducts.

Novel guaiacolethylamine synthetics primarily include the following:

Compound 1 . . . 1-[(4-allyl-2-methoxy)phenoxy}-3-[(2-methoxy phenoxyethyl)amino}-propanol; abbreviated as eugenodilol;

compound 2 . . . 1-[(4-propenoic acid ethyl ester-2-methoxy) phenoxy]-3-[(2-methoxyphenoxyethyl) amino]-propanol; abbreviated as ferulidilol;

compound 3 . . . 1-[4-nonanamide-2-methoxy)phenoxy]-3-[(2-methoxyphenoxy ethyl)amino]-propanol, abbreviated as capsinodilol;

compound 4 . . . 1-[(4-propenyl-2-methoxy)-phenoxy]-3-[(2-methoxyphenoxyethyl)amino]-propanol; abbreviated as isoeugenodilol;

compound 5 . . . -[4-(2-hydroxy-3-(4-oxyethylamino-3-methoxycinnamic cid)propoxy)-3-methoxy]-1-propylenyl benzene.

compound 6 . . . N-[4-(2-hydroxy-3-(4-oxyethylamino-3-methoxybenzoid acid)propoxy)-3-methoxy benzyl]-nonanamide.

compound 7 . . . N-[4-(2-hydroxy-3-(4-oxyethylamino-3-methoxybenzoic acid)propoxy)-3-methoxy]-1-propenylbezene.

compound 8 . . . N-[4-(2-hydroxy-3-(4-oxyethylamino-3-methoxycinnamic acid)propoxy)-3-methoxy benzyl]-nonanmide.

compound 9 . . . (N-[4-(2-hydroxy-3-(1-oxyethylamino-4-oxyacetic acid benzene)propoxy)-3-methoxy]-1-propenyl benzene.

compound 10 . . . N-[4-(4-ethylamino-1-oxyacetic acid ester benzene.

Upon crystallizing the Formula I synthetic compounds or the intermediate products, the melting points(mp) are taken, or derivative products obtained through purification process are tested respectively for physical/chemical values through element analysis, material spectrum(MS), infra-red spectrum (IR), hydrogen magnetic resonance spectrum($^1$H—NMR, $CDCl_3$) and its ultra-violet absorption to demonstrate that these synthetic compounds possess precise structures.

Different dosage of the synthetic compounds 1~4(1,0, 1.5, 3.0 mg/kg) can make the rate of heart beat appear to decline relative to the dosages given and their effectiveness have sustained for more than an hour. In terms of the blood pressure, all exhibit a continuous reduction trend in the blood pressure. The contraction generated from injecting 10 $\mu$M of L-phenylephrine into segregated guinea pig's pulmonary artery becomes a relaxation following the dosage of the synthetic compounds 1~4, as shown in Table 2, and the signs are related to the dosage administered. Cumulatively injecting the segregated guinea pig's right auricle and left auricle with isoproterenol may increase the pulsating rate of the right auricle and the contraction of the left auricle; yet when the concentrations of the synthetic compounds 1~4 are at $10^{-7}$ M, $10^{-6}$ M, and $10^{-5}$M, their reactions toward isoproterenol appear to be in competitive suppression. The Schild plot in Table 3 provides the $pA_2$ values for the resistance of synthetic compounds 1~4 toward isoproterenol in accelerating the pulsation of the right auricle and the contraction of the left auricle.

TABLE 1

Hypotensive effects of intravenous injection of guaiacoxypropanolamines in pentobarbital-anesthetized normotensive rats.
Blood pressure change (mmHg)

| Dose\Compound | 1 mg/kg | 1.5 mg/kg | 3 mg/kg |
|---|---|---|---|
| 1 | −23.1 ± 4.5 | −30.1 ± 3.6 | −38.1 ± 5.1 |
| 2 | −37.5 ± 5.2 | −44.2 ± 8.0 | −52.4 ± 4.5 |

TABLE 1-continued

Hypotensive effects of intravenous injection of guaiacoxypropanolamines in pentobarbital-anesthetized normotensive rats.
Blood pressure change (mmHg)

| Dose\Compound | 1 mg/kg | 1.5 mg/kg | 3 mg/kg |
|---|---|---|---|
| 3 | −32.6 ± 5.5 | −41.7 ± 4.0 | −52.0 ± 8.0 |
| 4 | −24.9 ± 3.2 | −29.5 ± 5.1 | −36.4 ± 7.2 |

Data were expressed as mean ± S.E. (n=6)

TABLE 2

The percentage of guaiacoxypropanolamines produced vascular smooth muscle relaxation in isolated guinea pig thoracic aorta.

| Conc.\Compound | $10^{-4}$ M | $10^{-5}$ M | $10^{-6}$ M |
|---|---|---|---|
| 1 | −62.8 ± 8.7[a] | −51.7 ± 6.8 | −39.7 ± 9.1 |
| 2 | −56.7 ± 5.1 | −42.1 ± 9.1 | −35.9 ± 7.9 |
| 3 | −55.1 ± 7.4 | −40.7 ± 8.4 | −34.5 ± 4.2 |
| 4 | −38.1 ± 6.5 | −30.1 ± 3.6 | −23.4 ± 3.7 |

[a]Each datum indicates the percentage of relaxation after application of test compounds in comparison with the basal value.

Data were expressed as mean ± S.E. (n=6)

Upon adding various definitives to the synthetic compounds proposed by this invention, such as aliphatic magnesium, corn starch, starch, lactose, propenolamines, ethanol, glycerine, or with diluents, lubricants, disintegrants, binders, or with coloring, sweetener tablets or other solidified forms may be formed, while by adding alkaline buffers such as phosphoric acid to adjust the pH values, injection solutions, other solutions and various medications may be obtained. Among which, the solidified medications include tablets, powders, capsules, oral dissolving tablets, and drops. The medications are also combined into effective injection solutions such as eye drops, and other liquefied prescriptive medications. Dosage prescribed may be adjusted according to the requirements of the symptoms, and are generally prescribed in 50 mg to 300 mg per person, three times a day.

Examination of Pharmaceutical Effectiveness
Examination of the Effect on Heartbeat and Blood Pressure A male Wistar Strain, weighing 300~450 grams, is administered with 40 mg/kg of pentobarbital sodium via hypodermic syringe for anesthesia before implementing trachea dissection and inserting respiratory tube to ensure the animal maintains smooth breath during operation, while also facilitating emergency rescue. The tube insertion is done with a polyethylene tube (PE50), with inner diameter of 0.85 mm and outer diameter of 0.97 mm, on the femoral vein to facilitate administering medication during the experiment; a 3-way stopcock is used by connecting one end to the medicated bottle, while the other end is connected to the saline solution bottle, thus some saline solution can be injected right after administering the medication to prevent the medication from lingering in the polyethylene tube (PE50) that may affect the accuracy of the experiment. The left artery is also inserted with the polyethylene tube(PE50) by using the same 3-way stopcock with one end connected to heparin solution as the polyethylene tube (PE50) is equipped with a valve to clear any blockage in the path; the other end is connected to disposable diaphgram dome (TA1019), which is then connected to the data converter, and through an amplifier, and then finally through the recorder to record the medication's impact on the male Wistar Strain's blood pressure and heartbeat. The Wistar Strain is given different dosages of test medication in 1.0, 1.5, 3.0 mg/kg respectively through intravenous injection to examine the medication's effects on heartbeat and blood pressure.

Results

A wistar Strain, with normal blood pressure, is given pentobarbital sodium anesthesia and is injected with different dosages of test medication through intravenous injection to observe the impacts on heartbeat and blood pressure. The results are shown in Table 1, different dosages, 1.0, 1.5, 3.0 mg/kg of synthetic compounds 1~4 can all regulate the rate of heartbeat with distinct decline in relation to the dosage while in terms of period of effectiveness, all were sustained over an hour; in terms of blood pressure, continuous blood pressure reduction is also found.

Evaluation of Relaxation of Blood Vein That is Detached From Guinea Pig's Body

A 300–450 gram guinea pig is obtained, and forcefully hit at the head, and blood drained from the artery at the neck to quickly retrieve the main chest artery, which is placed in chilled Kreb solution and the fatty tissue clung to the vicinity of the blood vein is carefully removed, and then the main chest artery is trimmed to a circular shape of approximately 5 mm. Two S-shaped platinum threads are used to stabilize the top and bottom of the main artery before placing it in a 10-milliliter organ tank with 95% oxygen and 5% carbon dioxide mixed gas. One end is connected to the bottom of the organ tank, and the other end connected to the force transducer, and a recorder is used to record the isometric contraction. The specimen is given one gram of tension, and after balancing for 60 minutes, 10 $\mu$M of phenylephrine is prescribed to test the vivacity of the main chest artery. Upon balancing and the phenylephrine rinsed off, 10 $\mu$M of phenylephrine is used again to achieve the maximum contraction. And upon balancing, different concentration of synthetic testing compounds are used, $10^{-5}$ M, $10^{-6}$ M, or $10^{-7}$ M, to observe the suppressing effects resulted from different concentrations of synthetic testing compounds.

Results

The contraction effects generated by giving 10 $\mu$M of L-phenylephrine in the primary artery detached from a guinea pig will become a relaxation effect when $10^{-6}$, $10^{-5}$, and $10^{-4}$ M synthetic compounds are introduced, as shown in Table-2, while a correlation to dosage is also established.

Examination of the Suppressing Effect on $\beta_1$Adrenergic Response (1) Experiment on Detached Guinea Pig's Right Auricle A 300~450 gram guinea pig is obtained and hit forcefully at the head to put it into comatose, the artery at the neck is cut to release the blood, then the chest is immediately cut open, and the heart quickly retrieved and placed in Krebs solution that is connected to mixed gas(95% oxygen, 5% carbon dioxide), and the left, right auricles separated. The right auricle, which is pulsating in reflex action, is pinned down on both ends by a frog-heart tweezer, and one end stabilized at the bottom and placed in an organ rinser filled with 10 milliliter of Krebs solution with the mixed gas, and the temperature maintained at 32.5□; the other end is connected to the force transducer, and the isometric contractions and pulsating frequency are recorded through the Coulbourn At-High-Speed Videograph. The specimen is given tension between 100–150 milligrams, and upon balancing, the following experiment is conducted:

(a) Completion of the Cumulative Concentration-Response Curves

In order to evaluate the degree of vivacity of the $\beta$-blockade on the synthetic compounds, for each detached auricle in reflex pulsation, upon balancing(approximately 60 minutes), the cumulative-concentration curve of the $\beta$-agonist isoproterenol is completed twice separately. The experiment is designed as follows: <1>The first curve indicates direct application of isoproterenol from low concentration to high using 0.5 log unit to gradually increase until it reaches the maximum reaction; this is the control unit. <2>the second curve is the experimental unit. Different concentrations of synthetic testing compounds($10^{-7}$ M, $10^{-6}$ M, or $10^{-5}$ M), from low concentration to high, are given 30 minutes to react before isoproterenol is used to complete the cumulative prescription. The $EC_{50}$ value is obtained from observation of the suppressing effects generated from different concentrations of synthetic testing compounds.

(b) Calculation for $pA_2$ Value

According to the method used by Arunlakshana and Schild in 1959, the corresponding values of the synthetic testing compounds are used as the horizontal coordinate, and the corresponding values on the first derivative of the dose ratio are used as the vertical coordination, the values obtains are graphed and linear regression is implemented to obtain a regressed straight-line horizontal coordinate's extracted distance value, which is the $pA_2$ value for this particular synthetic testing compound.

(2) Experiment on Detached Guinea Pig's Left Auricle

The left auricle that does not pulsate voluntarily is taken from the previous experiment(in which the guinea pig's detached right auricle is taken) and placed under identical condition with square-shaped frequency slightly larger than the threshold voltage by approximately 1 volt of bandwidth 5 msec to stimulate the left auricle to induce contracting reaction. The stimulating frequency is 0.5 Hz, resting tension is 0.5 grams. Upon balancing(approximately 50 minutes) the following experiment is conducted;

(a) Completion of the cumulative concentration-response curves, which is similar to the experimenting methods use on the same detached right auricle.

(b) The calculation of $pA_2$ value is same as the calculation method used in the experiment of the detached right auricle.

Results of the Suppressing Effect on the $\beta_1$ Adrenergic Response

Cumulative prescription of isoproterenol on the right auricle and the left auricle of a guinea pig may increase the auricular beating frequency of the right auricle and the contractibility of the left auricle, yet the concentrations of the synthetic compounds 1~4 at $10^{-7}$, $10^{-6}$, and $10^{-5}$M may competitively suppress the function of isoproterenol. Schild plot in Table-3 reveals the pA2 value on the synthetic compounds 1~4 in resisting the effects of isoproterenol on the pulsating rate of the right auricle and the contracting function of the left auricle.

TABLE 3

$\alpha/\beta$-adrenoceptor blocking potency of guaiacoxypropanolamines in the isolated guinea-pig tissues. The $PA_2$ values were calculated from individual Schild plots by regression analysis.

| $PA_2$ value*\ Compound | $\beta_1$ right atrium/left atrium | $\beta_2$ | $\alpha$ |
|---|---|---|---|
| 1 | 7.83/7.95 | 6.59 | 8.12 |
| 2 | 8.02/8.16 | 7.05 | 7.95 |

TABLE 3-continued

| | | | |
|---|---|---|---|
| 3 | 7.80/7.61 | 6.81 | 7.12 |
| 4 | 7.63/7.89 | 6.13 | 7.20 |

*Each $PA_2$ value was the mean ± S.E. of six to eight experiment results.

Examination of the Suppressing Effect on $\beta_2$ Adrenergic Response

300–450 gram guinea pig is obtained, and 5 mg/kg reserpine is injected on the belly 18~24 hours prior to the experiment. Upon hitting the guinea pig into comatose, the artery at the neck is cut and the blood released, and the chest is immediately cut open and the respiratory tract (approximately 4 centimeters long) is taken along the neck and placed in a cultivation dish containing Krems solution at room temperature and connected to mixed gas of 95% oxygen and 5% carbon dioxide. The surrounding tissues are carefully removed, then the respiratory tract is cut to spiral shape that contains 3 to 4 bone coils at each turn, and then cut in two halves, with the two sides clamped by the frog-heart tweezer; one end is stabilized at the bottom and placed in the organ rinser filled with 20 ml of Krebs solution with mixed gas and the temperature maintained at 32° C.; the other side is connected to the force transducer, and even-length isometric contraction is recorded through the Coulbourn At-High-Speed Videograph. The sample is given 2 grams of tension, and upon balancing, the following experiment is conducted.

(a) Cumulative Concentration-Response Curve

The respiratory tract used in the experiment is first balanced (approximately one hour) to derive a reflex tension, and then for each half of the respiratory tract, cumulative concentration-response curve for the isoproterenol is completed twice. In the first curve, no synthetic testing compound is added, and is used as the control unit; in the second curve, the synthetic compound first added for an hour before implementing the cumulative concentration-response curve, which is the experimental unit.

(b) Calculation of pA2 Value

It is same as the calculation method used in the experiment of detached right auricle.

Results of the Medication on the β2 Adrenergic Response

Cumulative prescription of isoproterenol on the detached respiratory tract, with reflex tension, derived from the guinea pig may cause the respiratory tract's tension to generate relaxing effect; when the concentration of the synthetic compound is at $10^{-6}$ M, $10^{-5}$ M, and $10^{-4}$ M, it may competitively suppress the effect of isoproterenol. Then Schild plot in Table 3 reveals the pA2 value derived from the relaxing effect in isoproterenol resistance to the test medication used on the detached respiratory tract.

Examination of the Suppressing Effect of α Adrenergic Response (a) Cumulative Concentration-Response Curve:

Same as the blood vein relaxation experiment, detached primary artery taken from the guinea pig is given 1 gram of tension, and upon balancing for 60 minutes, L-phenylephrine is administered directly from low concentration to high using 0.5 log unit to gradually increase until the maximum reaction is reached, and this act as the control unit. Then different concentrations of the synthetic testing compound, $10^{-7}$ M, $10^{-6}$ M, or $10^{-5}$ M, are used, and upon 30 minutes of reaction, L-phenylephrine is used again to complete the cumulative dose. The $EC_{50}$ value may be obtained from observation of the suppressing effects caused by different concentrations of the synthetic testing compound.

(b) Calculation of $pA_2$

It is same as the calculation method used in the experiment of the detached right auricle.

Results of the Suppressing Effect of a Adrenergic Response

Cumulative prescription of L-phenylephrine on the guinea pig's detached primary chest artery may induce the blood vein to generate contraction; synthetic testing compound at concentrations of $10^{-6}$ M, $10^{-5}$ M and $10^{-4}$ M, may competitively suppress the functions of L-phenylephrine. Then the Schild plot in Table 3 reveals the pA2 value derived from the contracting effect of the test medications' resistance against L-phenylephrine used on the detached blood vein.

EXAMPLE 1

The Compounding of Epoxide 8 g of sodium hydroxide is dissolved in 100 ml of absolute ethyl alcohol, and 1 molar of 4-hydroxy-3-methoxy-1-propenylbezene is dissolved in the aforementioned solution that contains sodium hydroxide and ethyl alcohol as it is stirred in room temperature. 5 molar of epichlorohydrine is then added at room temperature for reaction, and a TLC is used to ascertain whether the reaction has been completed. Upon completion of reaction, pressure reducing and evaporation are implemented, and the liquid concentrate is filled into the silicone tube. By utilizing Hexane: ethyl acetate=1: 9 as the diluent for separation, a white coarse crystallization is obtained. Hexane is used repeatedly for re-crystallization to derive at purified N-[4-(2,3-epoxy-propoxy)-3-methoxy]-1-propenybenzene.

(N-[4-(2,3-epoxypropoxy)-3-methoxy]-1-propenyl benzene)

$^1$H—NMR(CDCl$_3$) δ 1.846~1.886(d, 3H, Ar—CH=CH—CH$_3$), 2.76~2.92(m,2H, Ar—O—CH$_2$—HCΔCH$_2$),3.34~3.42(m, 1H, Ar—O—CH$_2$—HCΔCH$_2$), 3.882(s,3H, Ar—O—CH$_3$),4.05~4.09(t, 4H, Ar—O—CH$_2$—), 6.02~6.41(m, 1H, Ar—CH=CH—CH$_3$), 6.842~6.893(m, 3H, Ar—H),7.262(s, 1H, Ar—CH=CH—CH$_3$).

MS m/s:220(Scan EI$^+$). Anal. (C$_{13}$H$_{16}$O$_3$) (C,H,N)

EXAMPLE 2

One mole of ferulic acid is added to excess moisture-free ethyl alcohol and heated to boiling point for 48 hours. A small amount of sulfuric acid is added prior to heating as a catalyst. TLC is used to ascertain whether the reaction has been completed. Upon complete reaction, sodium hydroxide solution is added and the pH balance is adjusted to neutrality. Upon pressurized reduction, excess methanol is removed to derive at a purified 4-hydroxy-3-methoxycinnamic acid ethyl ester.

0.2 mole of 4-hydroxy-3-methoxycinnamic acid ethyl ester and 0.4 mole of ethylene dibromide are placed in a tri-neck bottle for heating until boiling point. After stirring, 125 ml of 1.6 N sodium hydroxide is added within 30 minutes, and it is heated and stirred until separate layers are formed. Heating is carried out overnight and TLC is used to ascertain whether the reaction has been completed. Chloroform is applied repeatedly to extract an organic layer; 300 grams of 2N sodium hydroxide is used to rinse the organic layer. Moisture-free magnesium sulfate is added and left overnight. Upon filtrating and pressurized reduction, silicone filled tubes are used for separation, diluent of hexane: ethyl acetate=9:1 is used to derive at the byproduct 4-oxyethylbromide-3-methoxycinnamic acid ethyl ester.

(4-oxyethylbromide-3-methoxycinnamic acid ethyl ester)

$^1$H—NMR(CDCl$_3$)

δ 1.313~1.361(t, 3H, Ar—CH=CH—COO—CH$_2$—CH$_3$), 3.646~3.690(t, 2H, Ar—O—CH$_2$—CH$_2$—Br), 3.901 (s,3H, Ar—O—CH$_3$), 4.225~4.297(m, 2H, Ar—O—CH$_2$—CH$_2$—Br), 4.338~4.383(t, 2H, Ar—CH=CH—COO—CH$_2$—CH$_3$), 6.296~6.349(d, 1H, Ar—CH=CH—COO—CH$_2$—CH$_3$), 6.873~7.262(m, 3H, Ar—H), 7.595~7.647(d, 1H, Ar—CH=CH—COO—CH$_2$—CH$_3$),

MS m/s:328(Scan EI$^+$), mp:76.1~77.6 °C Anal.(C$_{14}$H$_{17}$O$_4$Br) (C,H,N)

UV(CH$_3$OH) λmax(log ε): 292(4.27), 320(4.33)nm.

Upon mixing equal molars of 4-oxyethylbromide-3-methoxy cinnamic acid ethyl ester, potassium phthalimide, dimthylformamide is dissolved, and the temperature is brought to 55° C. in 5 minutes and maintained for 30 minutes before reducing it to room temperature. Chloroform used to extract the organic layer, 0.2M sodium hydroxide is added for rinsing; moisture-free magnesium sulfate is added and left overnight. Upon filtrating and pressurized reduction, recrystallization will produce the byproduct 4-oxyethyl phthalimide-3-methoxycinnamic acid ethyl ester.

(4-oxyethylphthalimide-3-methoxy cinnamic acid ethyl ester)

$^1$H—NMR (CDCl$_3$) δ 1.304~1.352(t, 3H, Ar—CH=CH—COO—CH$_2$—CH$_3$), 3.796(s, 3H, Ar—O—CH$_3$),4.120~4.160(t, 2H, Ar—O—CH$_2$—CH$_2$—N—), 4.216~4.250(m, 2H, Ar—O—CH$_2$—CH$_2$—N—), 4.263~4.334 (m, 2H, Ar—CH=CH—COO—CH$_2$—CH$_3$), 6.259~6.313(m, 1H, Ar—CH=CH—COO—CH$_2$—CH$_3$), 6.902~7.880(m, 7H, Ar—H), 7.563~7.617(m, 1H, Ar—CH=CH—COO—CH$_2$—CH$_3$),

MS m/s:395(Scan EI$^+$), mp:98.9~101.1°C Anal. (C$_{22}$H$_{21}$O$_6$N) (C,H,N).

UV (CH$_3$OH) λmax (log ε): 295(4.22), 321(4.27)nm.

Equal molars of 4-oxyethylphthalimide-3-methoxy cinnamic acid ethyl ester and hydrazine hydrate are dissolved in absolute ethyl, which is heated to boiling point for 45 minutes. Appropriate amount of 18% hydrochloric acid is added to generate white residue. Upon pressurized reduction, 20% sodium hydroxide is used for rinsing. Chloroform is used to extract the organic layer, and moisture-free magnesium sulfate is added and left overnight. Upon filtrating and pressurized reduction, 4-oxythylamine-3-methoxy cinnamic acide ethyl ester is derived.

(4-oxyethylamine-3-methoxy cinnamic acid ethyl ester)

$^1$H—NMR (CDCl$_3$) δ 1.313~1.361(t, 3H, Ar—CH=CH—COO—CH$_2$—CH$_3$), 3.122~3.157(t, 2H, Ar—O—CH$_2$—CH$_2$—NH$_2$), 3.892(s, 3H, Ar—O—CH$_3$), 4.060~4.094(m, 2H, Ar—O—CH$_2$—NH$_2$), 4.224~4.296 (m, 2H, Ar—CH=CH—COO—CH$_2$—CH$_3$), 6.286~6.339 (d, 1H, Ar—CH=CH—COO—CH$_2$—CH$_3$), 6.861~7.095 (m, 7H, Ar—H), 7.598~7.651 (d, 1H, Ar—CH=CH—COO—CH$_2$—CH$_3$),

MS m/s:265(Scan EI+), Anal.(C$_{14}$H$_{19}$O$_4$N) (C,H,N)

UV(CH$_3$OH)λmax (log ε): 300(4.23), 318(4.33)nm.

EXAMPLE 3

The Compounding of Synthetic Compound 5

Equal molar of oxythylamine-3-methoxy cinnamic acid ethyl ester and (N-[4-(2,3-epoxy-propoxy)-3-methoxy]-1-propenybenzene are dissolved in 100 ml of absolute ethyl alcohol, while the temperature is slightly raised to facilitate amine reaction; upon stirring, it is placed overnight to obtain white crystallization. Upon re-crystallization, using methanol purified (N-[4-(2-hydroxy-3-(4-oxyethyl amino-3-methoxy cinnamic acid ehtyl ester)propoxy)-3-methoxy]-1-propylenyl benzene is obtained.

(N-[4-(2-hydroxy-3-(4-oxyethylamino-3-methoxy cinnamic acid ethyl ester)propoxy)-3-methoxy]-l-propylenylbenzene $^1$H-NMR (CDCl$_3$) δ1.313~1.360(t, 3H, Ar—CH=CH—COO—CH$_2$~CH$_3$), 1.852~1.877(m, 3H, Ar—CH=CHCH$_3$), 2.2~2.7(b, 1H, NH), 887~2.952(m, 2H, Ar—O—CH$_2$—CH(OH)—CH$_2$—NH—), 3.100~3.135(t, 2H, Ar—O—CH$_2$—CH$_2$—N—), 3.838~3.856(d,6H, Ar—O—CH$_3$×2), 4.009~4.037(t, 4H, Ar—O—CH$_2$—CH$_2$—),4.145~4.180(m, 1H, Ar—O—CH$_2$~CH(OH)—CH$_2$—NH—), 4.225~4.295(m, 2H, Ar—CH=CH—COO—CH$_2$—CH$_3$), 6.123~6.169(m, 1H, Ar—CH=CH—CH$_3$), 6.280~6.304(d, 1H, Ar—CH=CH—CH$_3$), 6.333~6.356 (m, 1H, Ar—CH=CH—COO—), 6.837~7.083(m, 6H, Ar—H), 7.591~7.644(d, 1H, Ar—CH=CH—COO—), MS m/s:485(Scan EI$^+$), mp: 105.2~106.3° C. Anal.(C$_{27}$H$_{35}$O$_7$N) (C,H,N)

WV (CH$_3$OH) λmax (log ε): 261(4.49), 292(4.46), 311 (4.42)nm.

Appropriate amount of sodium hydroxide is dissolved in 0.1% acetone, and then N-[4-(2-hydroxy-3-(4-oxyethylamino -3-methoxycinnamic acid ethylester) propoxy)-3-methoxy}-1-propylenyl-benzene is added, which is heated until boiling point, and TLC is used to ascertain whether the reaction has been completed. The generated product is filled into silicone tubes by utilizing the ratio of ethyl acetate:methanol=1:1 as the diluent; upon purification, N-[4-(2-hydroxy-3-(4-oxy-ethylamino-3-methoxy-cinnamic acid) propoxy)-3methoxy]-1-propylenybenzene is obtained.

(N-[4-(2-hydroxy-3-(4-oxyethylamino-3-methoxy cinnamic acid)propoxy)-3-methoxy]-1-propylenyl benzene)

$^1$H—NMR (CDCl$_3$) δ1.7989~1.8328 (d, 3H, Ar—CH=CHCH$_3$), 2.9206(m, 2H, Ar—O—CH$_2$—CH (OH)—CH$_2$—NH—), 3.118~3.154(t, 2H, Ar—O—CH$_2$—CH$_2$—N—), 3.7596~3.7999(d,6H, Ar—O—CH$_3$×2), 3.8784(m, 4H, Ar—O—CH$_2$—CH$_2$—), 4.0343(m, 1H, Ar—O$_2$—CH$_2$—CH(OH)—CH$_2$—NH—), 6.0903~6.2002 (m, 1H, Ar—CH=CH—CH$_3$), 6.2844~6.2899 (d, 1H, Ar—CH=CH—CH$_3$), 6.3623~6.4401 (m, 1H, Ar—CH=CH—COO—), 6.8421~7.0938 (m, 6H, Ar—H), 7.2013~7.3319 (m, 1H, Ar—CH=CH—COO—),

MS m/s:457(Scan EI+), mp:157.1~157.9° C. Anal. (C$_{25}$H$_{31}$O$_7$N) (C,H,N)

UV(CH$_3$OH)λmax(log ε):264(4.35),297(4. 19)nm.

EXAMPLE 4

The Compounding of another Epoxide 10 grams(34 ml molar) of nonivamide is soaked in an appropriate amount of absolute alcohol, and an equal molar of sodium hydroxide is added for reaction at 80° C. for 3 hours; 5 times molar of epichlorohydrine is added for diffusion at room temperature for two hours. Upon reaction and pressurized reduction, it is heated until it dissolves and upon filtration, the filtered solution is placed overnight to derive at coarse crystals. Adding absolute alcohol for recrystallization, purified white cyrstals of N-[4-(2,3-epoxypropoxy)-3-methoxy -benzyl]-nonanamide are obtained.

EXAMPLE 5

Compounding of synthetic compound 6

5 g(14.3 molar) of purified N-[4-(2,3-epoxypropoxy)-3-methoxybenzyl]-nonanamide is dissolved in methanol before adding three times molar of 4-oxyethylamine-3-methoxybenzoic acid ethyl ester, and nitrogen gas is connected for diffusion at 55° C. for 4 hours. The solution derived from direct pressurized reduction is filtrated while it is still warm; it is placed
overnight to derive at coarsely crystal. Upon re-crystallization, using methanol purified N-[4-(2-hydroxy-3-(4-oxyethylamino-3-methoxybenzoic acid ethyl ester)propoxy)-3-methoxy}-1-propylenylbenzene is derived.

(N-[4-(2-hydroxy-3-(4-oxyethylamino-3-methoxy cinnamic acid ethyl ester)propoxy)-3-methoxy benzyl]-nonanamide)

δ: 0.87 (t, 3H, —$CH_3$); 1.28(m, 10H, —$(CH_2)_5$—);1.31(t, 3H, —$COCH_2$—$CH_3$); 1.65(t, 2H, —$CH_2$—); 2.20(t, 2H, —$CH_2$—); 2.55(br s, 1H, exchangeable, OH); 2.95(m, 2H, —$CH_2$—NH—$CH$—); 3.11(t, 2H, —CH(OH)—$CH_2$—NH—); 3.86(d, 6H, —$OCH_3 \times 2$); 4.01(s, 2H, Ar—O—$CH_2$—$CH_2$—); 4.16(m, 3H, Ar—O—$CH_2$—CH (OH)—); 4.27(dd, 2H, Ar—COO—$CH_2$—); 4.37(m, 2H, Ar—$CH_2$—); 5.81(s, 1H, —NH—); 6.30(d, 1H, Ar—CH=CH—); 6.78~7.05 (m, 6H, Ar×2); 7.60(d, 1H, Ar—CH=CH—), mp 122.5–123.5° C.

UV(MeOH) )λmax nm(logε): 228 (4.40), 285 (4.28), 320 (4.32).

MS m/s: 615($M^-$). Anal. $C_{34}H_{50}N_2O_8$.

The purified N-[4-(2-hydroxy-3-(4-oxyethylamino-3-methoxybenzoic acid ethyl ester)propoxy)-3-methoxybenzyl}-nonanamide is dissolved in sodium hydroxide-acetone solution, is stirred while being heated until 80° C. to obtain reaction for two hours. The solution obtained is directly pressurized to reduce, and left to derive at coarse crystallization; using methanol for re-crystallization until the white crystallization, N-[4-(2-hydroxy-3-(4-oxyethylamino-3-methoxybenzoid acid)propoxy)-3-methoxy benzyl]nonan-amide, is obtained.

N-[4-(2-hydroxy-3-(4-oxyethylamino-3-methoxy cinnamic acid)propoxy)-3-methoxy benzyl]-nonanamide)

$^1$H—NMR (DMSO) δ: 0.85 (t, 3H, —$CH_3$); 1.25 (m, 10H, —$(CH_2)5$—); 1.51 (t, 2H, —$CH_2$—); 1.84 (br s, 1H, exchangeable, OH); 2.11 (t, 2H, —$CH_2$—); 2.75 (m, 2H, —$CH_2$—NH —$CH_2$—); 2.91 (t, 2H, —CH(OH)—$CH_2$—NH—); 3.80 (d, 6H, —$OCH_3 \times 2$); 3.86 (s, 2H, Ar—O—$CH_2$—$CH_2$—); 4.03 (m, 3H, Ar—O—$CH_2$—CH (OH)—); 4.18 (d, 2H, Ar—$CH_2$—); 4.98 (s, 1H, —NH—); 6.55 (d, 1H, Ar—CH=CH—); 6.72~7.12 (m, 6H, Ar×2); 7.57 (d, 1H, Ar—CH=CH—); 8.21 (s, 1H, —COOH), mp 135–137° C.

WV(MeOH) )λmax (logε): 229(4.30),322 (4.20).

MS m/s: 586 (M-). Anal. $C_{32}H_{46}N_2O_8$

EXAMPLE 6

One mole of vanillic acid is added to excess moisture-free ethanol, upon heating to boiling point for 48 hours, while a small amount of sulfur is added prior to heating as the catalyst. TLC is used to ascertain whether the reaction has been completed. Upon complete reaction, sodium hydroxide solution is added to adjust the pH value to neutral. Upon pressurized reduction, methanol is used for re-crystallization to derive 4-hydroxy-3-methoxybenzoid acid ethyl ester.

0.2 mole of 4-hydroxy-3-methoxybenzoid acid ethyl ester and 0.4 mole of ethylene dibromide are placed in a tri-neck bottle for heating until boiling point; upon stirring and after 30 minutes, 125 ml of 1.6 M sodium hydroxide is then added, and heated and stirred to form layers. Chloroform is used to extract the organic layer, and 300 ml of 2M sodium hydroxide is used to rinse the organic layer; moisture-free magnesium sulfate is then added and left overnight. Upon filtration and pressurized reduction, it is filled in the silicone tube for separation, hexane: ethyl acetate =9:1 is used as the diluent to obtain the byproduct of 4-oxyethylbromide-3-methoxybenzoic acid ethyl ester.

(4-oxyethylbromide-3-methoxybenzoic acid ethyl ester)

$^1$H—NMR ($CDCl_3$) δ:1.370~1.417(t, 3H, Ar—COO—$CH_2$—$CH_3$), 3.665~3.709(t, 2H, Ar—O—$CH_2$—$CH_2$—Br), 3.931(s,3H, Ar—O—$CH_3$), 4.330~4.390(t, 2H, Ar—O—$CH_2$—$CH_2$—Br), 4.401~4.413(m, 2H, Ar—COO—$CH_2$—$CH_3$), 6.887~7.680(m, 3H, Ar—H), mp:70.9~71.2° C.

MS m/s:302(Scan EI$^+$), Anal. ($C_{12}H_{15}O_4Br$) (C,H,N)

UV($CH_3OH$)λmax(log F): 256(4.08), 291(3.77)nm,

Equal molar of 4-oxyethylbromide-3-methoxybenzoic acid ethyl ester is mixed with potassium phthalimide, and dissolved with dimthylformamide; the temperature is raised to 55° C. within 5 minutes, and maintained for 30 minutes before reducing it to room temperature. Chloroform is used to extract the organic layer, and 0.2N sodium hydroxide is used for rinsing, upon adding moisture-free magnesium sulfate, it is left overnight. Upon filtration, pressurized reduction, re-crystallization, a byproduct 4-oxyethylphthalimide-3-methoxybenzoic acid ethyl ester is obtained.

(4-oxyethylphthalimide-3-methoxy benzoic acid ethyl ester)

$^1$H—NMR($CDCl_3$) δ:1.353~1.399 (t, 3H, Ar—COO—$CH_2$—$CH_3$), 3.826 (s, 3H, Ar—O—$CH_3$), 4.137~4.178 (t, 4H, Ar—O—$CH_2$—$CH_2$—N—), 4.307~4.317 (m, 2H, Ar—O—$CH_2$—$CH_2$—N—), 4.330~4.354 (m, 2H, Ar—COO—$CH_2$—$CH_3$), 6.913 ~7.884 (m, 7H, Ar—H),

MS m/s:369(Scan EI$^+$), mp:157.1~158.2° C. Anal.($C_{20}H_{19}O_6N$)(C,H,N)

UV($CH_3OH$)λmax(log F): 257(4.16), 292(3.51)nm.

Equal molar of 4-oxyethylphthalimide-3-methoxybenzoic acid ethyl ester and hydrazine hydrate are obtained and dissolved in absolute ethanol before heating to boiling point for 45 minutes. Appropriate amount of 18% hydrochloric acid is used to general white residue. Filtration method is used to eliminate the white residue, and rinsing is done with ethanol to obtain filtrated solution. Upon pressurized reduction and rinsing with 20% sodium hydroxide, Chloroform is used to extract the organic layer before adding moisture-free magnesium sulfate and placed overnight. Upon filtration, pressurized reduction, 4-oxyethylamine-3-methoxybenzoic acid ethyl ester is derived.

(4-oxyethylamine-3-methoxybenzoic acid ethyl ester)

$^1$H—NMR (CDCl$_3$)

δ:1.360~1.407 (t, 3H, Ar—COO—CH$_2$—CH$_3$), 3.138~3.172 (t, 2H, Ar—O—CH$_2$—CH$_2$—NH$_2$), 3.883~3.910 (d, 6H, Ar—O—CH$_3$), 4.079~4.113 (m, 2H, Ar—O—CH$_2$—NH$_2$), 4.317~4.388 (m, 2H, Ar—COO—CH$_2$—CH$_3$), 6.869~7.670 (m, 3H, Ar—H),

MS m/s:239(Scan EI$^+$), Anal. (C$_{12}$H$_{17}$O$_4$N) (C,H,N)

UV (CH$_3$OH) λmax (log εF): 256(3.99), 289(3.73)nm,

EXAMPLE 7

The Compounding of Synthetic Compound 7

Purified N-[4-(2,3-epoxypropoxy)-3-methoxy]-1-propenylbenzene is dissolved in 100 ml of absolute ethanol before adding 4-oxyethylamine-3-methoxybenzoic acid ethyl ester, and the temperature is slightly raised to proceed with amines reaction. Upon stirring, it is placed overnight to obtain solidified white crystallization. Methyl alcohol is used for re-crystallization to obtain 4-(2-hydroxy-3-(4-oxyethyl amino-3-methoxy-benzoic acid ethyl ester)propoxy)-3-methoxy]-1-propenylbenzene.

(N-[4-(2-hydroxy-3-(4-oxyethylamino-3-methoxy benzoic acid ethyl ester)propoxy)-3-methoxy benzyl]-nonanamide)

$^1$H—NMR (CDCl$_3$) δ: 0.87 (t, 3H, —CH$_3$); 1.27 (m, 10H, —(CH$_2$)$_5$—); 1.39 (t, 3H, —CO CH$_2$—CH$_3$); 1.65 (t, 2H, —CH$_2$—); 2.01 (t, 2H, —CH$_2$—); 2.50 (br s, 1H, exchangeable, OH); 2.91 (m, 2H, —CH$_2$—NH—CH$_2$—); 3.14 (t, 2H, —CH(OH)—CH$_2$—NH—); 3.82 (d,6H, —OCH$_3$×2); 4.03 (t, 2H, Ar—O—CH$_2$—CH$_2$—); 4.10 (m, 1H, CH$_2$—CH(OH)—CH$_2$—); 4.19 (t, 2H, Ar—O—CH$_2$—CH(OH)—); 4.34 (m, 2H, Ar—COO—CH$_2$—); 4.37 (m, 2H, Ar—CH$_2$—); 5.71 (s, 1H, —NH—); 6.76~7.66 (m, 6H, Ar×2), mp 140–142° C.

MS m/s:588 (M$^-$). Anal. C$_{32}$H$_{48}$N$_2$O$_8$

UV(MeOH) λmax (log δ):223(4.46), 260(4.40).

Upon purification, the aforementioned synthetic compound is dissolved in sodium hydroxide solution that contains 10% acetone before heating to boiling point; TLC is used to ascertain whether the reaction has been completed. The product is filled in the silicone tube, using the ratio of ethyl acetate: ethyl alcohol=1:1 as the diluent for separation; upon purification, N-[4-(2-hydroxy-3-(4-oxyethylamino-3-methoxy benzoid acid) propoxy)-3-methoxy]-1-propenylbenzene is derived.

(N-[4-(2-hydroxy-3-(4-oxyethylamino-3-methoxy benzoic acid)propoxy)-3-methoxybenzyl]-nonanamide)

$^-$H—NMR(DMSO) δ:0.85 (t, 3H, —CH$_3$); 1.23 (s, 10H, —(CH$_2$)5—); 1.45 (t, 2H, —CH$_2$—); 1.95 (br s, 1H, exchangeable, OH); 2.11 (t, 2H, —CH$_2$—); 2.45 (m, 2H, —CH$_2$—NH—CH$_2$—); 2.96 (t, 2H, —CH(OH)—CH$_2$—NH—); 3.73 (d, 6H, —OCH$_3$×2); 3.87 (m, 3H, Ar—O—CH$_2$—CH (OH)—); 4.00 (t, 2H, Ar—O—CH$_2$—CH$_2$—); 4.18 (d, 2H, Ar—CH$_2$—); 5.08 (s, 1H, —NH—); 6.82~7.50 (m, 6H, Ar×2); 7.14 (s, 1H, —COOH), mp 148~150° C.

MS m/s: 560(M$^-$). Anal.C$_{30}$H$_{44}$N$_2$O$_8$

UV(MeOH) λmaxnm (log δ):230(4.21),281 (3.89).

EXAMPLE 8

The Compounding of Synthetic Compound 8

5 g(14.3 molar) of purified N-[4-(2,3-epoxypropoxy)-3-methoxybenzyl]-nonanamide is dissolved in moisture-free methanol before adding 3 times the molar of 4-oxyethyl amine-3-methoxy cinnamic acid ethyl ester, while nitrogen gas is connected at 55° C. to diffuse for reaction over 4 hours. The solution obtained from direct pressurized reduction is filtrated when it is still warm, and the crystallization obtained is mixed with methanol repeatedly filtrated solution is set aside overnight. The course for re-crystallization until purified white crystallization is formed, which is N-[4-(2-hydroxy-3-(4-oxyethylamino-3-methoxycinnamic acid ethyl ester)propoxy)-3-methoxybenzyl]nonanamide.

N-[4-(2-hydroxy-3-(4-oxyethylamino-3-methoxy benzoic acid ethyl ester)propoxy)-3-methoxy]-1-propylenylbenzene $^1$H—NMR (CDCl$_3$) ε1.366~1.414(t, 3H, Ar—COO—CH$_2$—CH$_3$), 1.853~1.879(d, 3H, Ar—CH=CHCH$_3$), 2.15~2.22(b, 1H, NH), 2.892~2.957(m, 2H, Ar—O—CH$_2$—CH(OH)—CH$_2$—NH—), 118~3.154(t, 2H, Ar—O—CH$_2$—CH$_2$—N—), 3.841~3.885(d, 6H, Ar—O—CH$_3$×2), 4.010~4.041 (t, 4H, Ar—O—CH$_2$—CH$_2$—), 4.170~4.204 (m, 1H, Ar—O—CH$_2$—CH(OH)—CH$_2$—NH—), 4.323~4.395(m, 2H, Ar—COO—CH$_2$—CH$_3$), 6.052~6.169 (m, 1H, Ar—CH=CH—CH$_3$), 6.303~6.358(d, 1H, Ar—CH=CH—CH$_3$), 6.838~7.670(m, 6H, Ar—H), MS m/s:459(Scan EI+), mp: 111.2~112.6° C. Anal.(C$_{25}$H$_{33}$O$_7$N)(C,H,N)

UV(CH$_3$OH)λmax(log ε): 217(4.45), 256(4.39)nm,

Upon dissolving the above mentioned purified synthetic compound in sodium hydroxide-acetone solution, it is stirred and heated to 80° C. for reaction over two hours. The solution obtained from the reaction is then directly pressurized and reduced, and upon setting aside, coarse crystallization is obtained. Methanol is used for re-crystallization until white crystallization is obtained, which is N-[4-(2-hydroxy-3-(4-oxyethylamino-3-methoxycinnamic acid) propoxy)-3-methoxy benzyl]-nonanamide.

N-[4-(2-hydroxy-3-(4-oxyethylamino-3-methoxy benzoic acid)propoxy)-3-methoxy]-1-propylenyl benzene $^1$H-NMR (CDCl$_3$) δ:1.7990~1.8349(d, 3H, Ar—CH=CHCH$_3$),2. 6~2.7344(m, 2H, Ar—O—CH$_2$—CH(OH)—CH$_2$—NH—), 2.8551~2.9148(t, 2H, Ar—O—CH$_2$—CH$_2$—N—), 7386~3.7618(d, 6H, Ar—O—CH$_3$×2), 3.8780~3.9018(t, 4H, Ar—O—CH$_2$—CH$_2$—), 3.9758~4.0309(m, 1H, Ar—O—CH$_2$—CH(OH)—CH$_2$—NH—), 6.0906~6.2003(m, 1H, Ar—CH=CH—CH$_3$), 6.2847~6.3708(d, 1H, Ar—CH=CH—CH$_3$), 6.8191~7.4945(m, 6H, Ar—H), MS m/s:43 1(Scan EI$^+$), Anal.(C$_{23}$H$_{29}$O$_7$N)(C,H,N)

UV(CH$_3$OH)λmax(log ε):254(3.90)nm

EXAMPLE 9

The Compounding of 2-(2-methylbenzoxy)ethylamide)

0.2 mole(22.4 ml) of guaiacol and 0.4 mole (34.6 ml) of ethylene dibromide are heated to 100° C. while stirring vigorously, and within 30 minutes, 125 ml of 1.6 N sodium hydroxide solution is added to continue the stirring and the pH value is adjusted to 7. Upon cooling, the mixed solution's organic layer is extracted with chloroform and rinsed with 2N sodium hydroxide before rising again with saturated sodium chloride solution and magnesium sulfate. Upon reduction, the solution is filled into the silicone tube for separation. Using the ratio of hexane: ethyl acetate=9:1 as the diluent, white crystallized product, 2-(2-methoxyphenoxy ethylbromide, is obtained.

36 g(0.156 ml) of 2-(methoxyphenoxy)ethylbromide and 27.3 grams (0.186 mole) of phthalimide are dissolved in 100 ml of dimethylacetamide, and stirred with heat for diffusion to 90° C. After 30 minutes, 10.45 g(0.186 mole) of potassium hydroxide is dissolved in 30 ml of methanol solution for heating and diffusing over 1.5 hours. Upon cooling, the mixed solution is poured into 300 ml of water. After filtrating the extracted solids, 200 ml of 10% potassium carbonate solution is added, and stirred with heat. The paste-like substance obtained is filtrated. After rinsing with tap water several times, moisture-free alcohol is used for re-crystallization until while crystallization is obtained.

21 grams(0.071 mole) of the above product and 3.55 grams (0.071 mole) of hydrazine hydrate are dissolved in 70 ml of moisture-free alcohol, and upon heating and diffusing for 45 minutes, 20 ml of 18% hydrochloric acid is added into the mixture to continue the diffusion for one hour before cooling. After filtration, the residue obtained from reduction is mixed with 20% of sodium hydroxide for alkalization. Chloroform is used for extraction, and upon filtration and pressurized reduction, it is filled into the silicone tube for separation, while using ethyl acetate as the diluent to obtain an oily product, i.e. 2-(2-methoxy-phenoxy)ethylamine.

EXAMPLE 10

The Compounding of Synthetic Compound 1

One mole of 4-hydroxy-3-methoxy-3-propenylbezene is added to a reactive bottle containing 900 ml of ethyl alcohol, while equal mole of sodium hydroxide is added, and heated to 70° C. for reaction over one hour before adding 5 times molar of epichlorohydrine to diffuse for two hours under the same conditions. Upon completing the reaction and pressurized reduction, the reduced concentrate is filled into the silicone tube, while using hexane: ethyl acetate=1:9 as the diluent to separate and derive at white crystallization.

0.03 mole of n-[4-(2,3-epoxypropoxy)-3-methoxy]-3-propenylbenzene and 5.0 grams (0.03 mole) of 2-(2-methoxy-phenoxy)ethylamine are dissolved in 30 ml of moisture-free alcohol, and stirred for 2 hours at room temperature before conducting amines reaction. After the mixed solution has been pressurized and reduced, the reduced concentrate is filled into the silicone tube for separation; and reduction is done to obtain white crystallized product. An appropriate amount of sodium hydroxide solution is dissolved in 0.1% of acetone, and the aforementioned white crystallized product is then dissolved, and heated to boiling point; TLC is used to ascertain whether the reaction has been completed. The product is filled into the silicone tube, while using the ratio of ethyl acetate: methanol=1:1 as the diluent; upon purification, 1-[(4-allyl-2-methoxy) phenoxy]-3-[(2-methoxy-phenoxyethyl)amino]-propanol is obtained.

(1-[(4-allyl-2-methoxy)phenoxy]-3- [(2-methoxy phenoxyethyl]amino]- propanol)

$^1$H—NMR (CDCl$_3$) δ:2.93–3.16(m, 4H, CH$_2$—NH—CH$_2$);3.31–3.34(d, 2H, Ar—CH$_2$);3.80–3.83 (m, 6H, OCH$_3$×2);4.00–4.03(m, 2H, Ar—OCH$_2$);4.13–4.19(m, 3H, Ar—OCH$_2$CH(OH));5.03–5.12(m, 2H, —CH=CH$_2$); 5.88–6.01(m, 1H, —CH=CH$_2$);6.68–7.00(m, 7H, Ar);

MS m/s:388 (Scan EI$^+$).

Anal.C$_{22}$H$_{29}$NO$_5$, mp. 46–48° C.

EXAMPLE 11

The Compounding of Synthetic Compound 3

0.03 mole of N-[4-(2,3-epoxypropoxy)-3-methoxy benzyl]-nonanamide and 0.09 mole of 2-(2-methoxyphenoxy)ethylamine are dissolved in 30 ml of moisture-free alcohol, and -stirred for 2 hours at room temperature for amines reaction. Upon pressurized reduction of the mixed solution, the concentrate is filled into the silicone tube for separation; upon reduction, white crystallization is obtained. An appropriate amount of sodium hydroxide is dissolved in 0.1% acetone before dissolving in the above mentioned white crystallization, and heating the solution to boiling point. TLC is used to ascertain whether the reaction has been completed. The product is filled into the silicone tube, while using the ratio of ethyl acetate: methanol=1:1 as the diluent for separation; upon purification, 1-[(4-nonanamide-2-ethoxy)phenoxy]-3-[2-methoxyphenoxyethyl) -amino]-propanol is obtained.

(1- [(4-nonanamide-2-methoxy)phenoxy]-3- [(2-methoxy phenoxyethyl]amino]-propanol)

$_1$H—NMR (CDCl$_3$) δ: 0.80–0.92(m, 3H, CH$_3$);1.27(s, 10H, CH$_2$×5); 1.58–1.72(m, 2H, CH$_2$);2.15–2.26(m, 2H, CH$_2$);2.78–3.11(m, 4H, CH$_2$—NH—CH$_2$); 3.82–3.84(m, 6H, OCH$_3$×2);3.98–4.02(m, 2H, Ar—OCH$_2$);4.06–4.12(m, 3H, Ar—OCH$_2$CH(OH));4.34–4.37(d, 2H, Ar—CH$_2$);5.76 (br, 1H, NH);6.74–6.91(m, 7H, Ar);

MS m/s: 517(Scan FAB$^+$). Anal.C$_{29}$H$_{44}$N$_2$O$_6$, mp. 138–139° C.

EXAMPLE 12

The Compounding of Synthetic Compound 2

One mole of Ferulic acid is obtained and added with small amount of sulfuric acid as the catalyst and excess moisture-free ethyl, and heating them to boiling point for 48 hours. TLC is used to ascertain whether the reaction has been completed. Upon complete reaction, sodium hydroxide solution is added to adjust the pH value to neutral; upon pressurized reduction, methanol is used for re-crystallization to obtain 4-hydroxy-3-methoxycinnamic acid ethyl ester.

One mole of the above described product is obtained and dissolved in 100 ml of absolute ethyl that contains sodium hydroxide, which is stirred at room temperature. 5 molar of epichlorohydrine is then added and stirred at room temperature for reaction. Upon complete reaction, pressurized reduction is implemented and the concentrate is filled into the silicone tube, while using hexane: ethyl acetate=1:9 as the diluent for separation to obtain coarse crystallization. Ethylene is repeatedly used for re-crystallization to obtain N-[4-(2,3-epoxypropoxy)-3-methoxy-cinnamic acid ethyl ester.

0.03 mole of N-[4-(2,3-epoxypropoxy)-3-methoxy-cinnamic acid ethyl ester and 0.03 mole of 2-(2-Methoxyphenoxy)ethyl- amine are dissolved in 30 ml of moisture-free alcohol, and stirred for two hours at room temperature for amines reaction. After the mixture is pressurized and reduced, the concentrate is filled into the silicone tube for separation; upon reduction, white crystallization is obtained. An appropriate amount of sodium hydroxide solution is dissolved in 0.1% acetone before dissolving the aforementioned white crystallization, and then the solution is heated to boiling point. TLC is used to ascertain whether the reaction has been completed. The product is filled into the silicone tube, using the ratio of ethyl acetate: methanol= 1:1 as the diluent for separation; upon purification, 1-[(4-propenoic acid ethyl ester -2-methoxy)phenoxy]-3-[(2-methoxyphenoxy ethyl) amino]-propanol is obtained.

(1-[(4-propenoic acid ethyl ester-2-methoxy) phenoxy] -3-[(2-methoxyphenoxy ethyl)amino]-propanol)

$^1$H-NMR (CDCl$_3$) δ: 1.30–1.37(m, 3H, CH$_3$);3.13–3.18 (m, 4H, CH$_2$—NH—CH$_2$);3.77–3.82(m, 6H, OCH$_3$×2); 4.06~4.08(d, 2H, Ar—OCH$_2$);4.15–4.19(m, 3H, Ar—OCH$_2$CH(OH)); 4.24–4.31 (COOCH$_2$);6.26–6.34(d, 1H, Ar—CH=CH); 6.86–7.09(m, 7H, Ar); 7.57–7.65 (d, 1H, Ar—CH=CH);

MS m/s: 446 (Scan EI$^+$). Anal. C$_{24}$H$_{31}$NO$_7$, mp. 94.6–96.4° C.

EXAMPLE 13
The Compounding of Synthetic Compound 4

Equal molar of N-[4-(2,3-epoxypropoxy)-3-methoxy]-1-propenylbenzene and 2-(2-Methoxyphenoxy)ethylamine are dissolved in 30 ml of moisture-free alcohol, and stirred for two hours at room temperature for amines reaction. After the mixture is pressurized and reduced, the concentrate is filled into the silicone tube for separation; upon reduction, while crystallization is obtained. An appropriate amount of sodium hydroxide is dissolved in 0.1% of acetone before dissolving the aforementioned white crystallization, which is then heated to boiling point; TLC is used to ascertain whether the reaction has been completed. The product is filled into the silicone tube, while using the ratio of ethyl acetate: methanol=1:1 as the diluent for separation; upon purification, 1-[(4-propenyl-2-methoxy)-phenoxy]-3-[(2-methoxyphenoxy ethyl)amino]-propanol is obtained.

(1- [(4-propenyl-2-methoxy)phenoxy]-3-[(2-methoxyphenoxyethyl)amino]-propanol)

$^-$H—NMR(CDCl$_3$) δ:1.11–1.25(m, 3H, CH$_3$);2.87–3.12 (m, 4H, CH$_2$—NH—CH$_2$); 3.84 (s, 6H, OCH$_3$×2);4.00–4.14 (m, 2H, Ar—OCH$_2$); 4.00–4.04(m, 2H, Ar—OCH$_2$); 4.13–4.16 (m, 3H, Ar—OCH$_2$CH(OH)); 6.04–6.37(m, 2H, —CH=CH); 6.84–6.95(m, 7H, Ar);

mp.90.2–91.6° C. MS m/s: 388(Scan EI$^+$). Anal.C$_{22}$H$_{29}$NO$_5$.

EXAMPLE 14
The Compounding of Synthetic Compound 9

0.2 mole of 1,4-dihydroxybenzene and equal mole of bromoacetic acid are heated to boiling point; TLC is used to ascertain whether the reaction has been completed. Upon complete reaction and pressurized reduction, it is filled into the silicone tube for separation, while using methanol : ethyl acetate=2:8 as the diluent to obtain the byproduct of 4-oxyacetic acid phenol.

0.4 mole of 4-oxyacetic acid phenol and 0.4 mole of ethylene dibromide are placed in tri-neck bottle for heating to boiling point before mixing in 125 ml of 1.6 M sodium hydroxide; TLC is used to ascertain whether the reaction has been completed. Chloroform is used to extract the organic layer, and 300 ml of 2N sodium hydroxide is used to rinse off the organic layer; moisture-free free magnesium sulfate is added before setting it aside overnight. Upon filtrating and pressurized reduction, the product is filled into the silicone tube for separation, while using hexane: ethyl acetate=9:1 as the diluent to obtain 4-oxyacetic acid phenoxyethylbromide.

Upon mixing 4-oxyacetic acid phenoxyethylbromide and equal molar of potassium phthalimide, it is dissolved in dimthyl-formamide before the temperature is raised to 55° C. within 5 minutes, which is continued for 30 minutes before reducing to room temperature. Chloroform is used to extract the organic layer, 0.2 N of sodium hydroxide is used for rinsing; moisture-free magnesium sulfate is added and set aside overnight. Upon filtration and pressurized reduction, recrystallization is done to obtain the byproduct of 4-oxyacetic acid phenoxy-ethylphthalimide.

Equal molar of 4-oxyacetic acid phenoxyethylphthalimide and hydrazine hydrate are dissolved in absolute ethyl before heating to boiling point and continued for 45 minutes. An appropriate amount of 18% hydrochloric acid is added to generate white residue. Filtrating method is used to eliminate the white residue; upon rinsing with ethyl to obtain the filtrated solution. Upon pressurized reduction, 20% of sodium hydroxide is used for rinsing; chloroform is used to extract the organic layer; moisture-free magnesium sulfate is added and left overnight. Upon filtration and pressurized reduction, 4-Oxyacetic acid phenoxy-ethylamine is obtained.

Mix N-[4-(2,3-epoxypropoxy)-3-methoxy]-1-propenyl-benzene and equal molar of 4-oxyacetic acid phenoxyethy-lamine and dissolve it in 100 ml of moisture-free alcohol, and stirred for two hours at room temperature for amines reaction. After the mixture has been pressurized and reduced, test is made to see if the reaction is complete. The production is set aside overnight; upon filtration and pressurized reduction, N-[4-(2-hydroxy-3-(4-oxyacetic acid phenoxyethyl-amino) propoxy)-3-methoxy]-1-propenylbenzene is obtained.

EXAMPLE 15 p-hydroxybenzaldehyde and equal molar of nitromethane are obtained and heated to boiling point; TLC is used to ascertain whether the reaction has been completed. Upon complete reaction and pressurized reduction, silicone tube is used for filling the product for separation, while using hexane: ethyl acetate =7:3 as the diluent to obtain the byproduct of 4-ethylnitro phenol.

4-ethylnitro phenol is obtained and mixed with appropriate zinc powder and acetic acid before dissolving in moisture-free alcohol, and upon heating to boiling point, TLC is used to ascertain whether the reaction has been completed. Upon complete reaction and pressurized reduction, the product is placed overnight to obtain 4-ethylamino-phenol. Equal molar of bromoacetic acid is added and heated to boiling point; TLC is used to ascertain whether the reaction has been completed. Upon complete reaction and pressurized reduction, the product is placed overnight to obtain byproduct 4-ethylamino-l-oxyacetic acid benzene.

EXAMPLE 16
The Compounding of Synthetic Compound 10

One mole of 4-oxyacetic acid phenol is obtained and adding small amount of sulfuric acid as the catalyst and excess moisture-free alcohol, heating is done until boiling point for 48 hours. Upon complete reaction, sodium hydroxide solution is added to adjust the pH value to neutral value. Upon pressurized reduction, methanol is used for re-crystallization to obtain 4-oxyacetic acid ethyl ester phenol.

0.2 mole of 4-oxyacetic acid ethyl ester phenol and 0.4 mole of ethylene dibromide are placed in a tri-neck bottle for heating until boiling point, and 125 ml of 1.6 N sodium hydrogen is added; TLC is used to ascertain whether the reaction has been completed. Chloroform is used to extract the organic layer, 300 ml of 2N sodium hydroxide is used to rinse off the organic layer; moisture-free magnesium sulfate is added and set aside overnight. Upon filtration and pressurized reduction, silicone filled tube is used for separation, while using hexane: ethyl acetate=9:1 as the diluent, 1-oxyethylbromide-4-oxyacetic acid ethyl ester benzene is obtained.

Mix 4-ethylamino-1-oxyacetic acid benzene and equal molar of 1-oxyethylbromide-4-oxyacetic acid ethyl ester benzene and dissolve it in 100 ml of moisture-free alcohol, which is then stirred for two hours at room temperature for amines reaction. After the mixture has been pressurized and reduced, test is conducted for complete reaction. The product is placed overnight; upon filtration and pressurized reduction, N-[4-(4-ethylamino-1-oxyacetic acid benzene)ethoxy]-1-oxyacetic acid ethyl ester benzene is obtained.

EXAMPLE 17

Tablet Form Prepared Formulation

| Tablet Form prepared formulation | |
| --- | --- |
| compound 1 | 50 mg |
| Lactose | 30 mg |
| Starch | 4 mg |
| magnesium stearate | 6 mg |
| Corn starch | 10 mg |

The prescription as above can be prepared a tablet form that contains compound 1

What is claimed is:

1. A guaiacoxypropanolamines compound of Formula I, shown as the following structure:

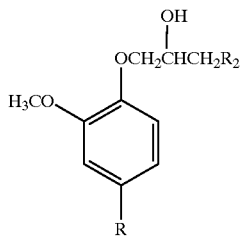

where R is $CH_2CH=CH_2$, $CH=CHCOOC_2H_3$, $CH=CHCH_3$ $CH_2NHCO(CH_2)_7CH_3$-

$R_2$ is

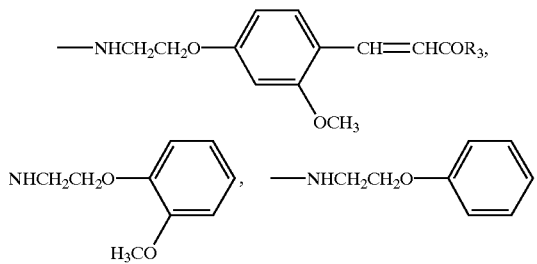

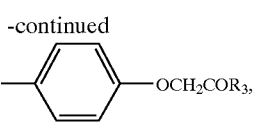

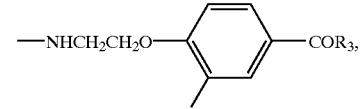

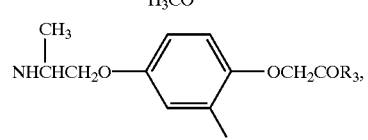

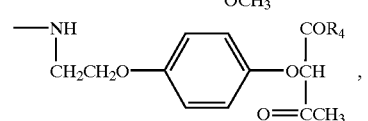

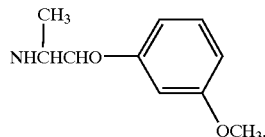

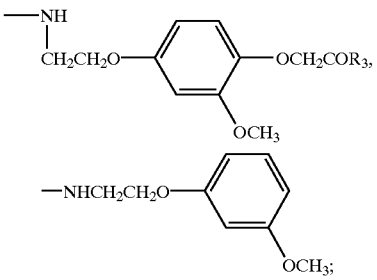

$R_3$ is

OH, $OCH_3$, $NHCH_2CH_2OCH_3$, $CH_2R_6$;

$R_4$ is $OCH_3$, $OC_2H_5$, $CH_2R_6$;

$R_6$ is $C_1$–$C_6$ Saturated Alkyl, $C_1$–$C_6$ Unsaturated Alkyl.

2. A pharmaceutical composition exhibiting α/β-adrenergic blocking activity comprises any compound according to claim 1 together with pharmaceutically acceptable carriers or diluents.

3. A compound of claim 1 wherein said compound is [(4-allyl-2-methoxy)phenoxy]-3-[2-methoxy phenoxyethyl)amino]-propanol.

4. A compound of claim 1 wherein said compound is [(4-nonanamide-2-methoxy)phenoxy]-3-[(2-methoxyphenoxyethyl)amino]-propanol.

5. A compound of claim 1 wherein said compound is 1-[(4-propenoic acid ethyl ester-2-methoxy)phenoxy]-3-[(2-methoxyphenoxy-ethyl)amino]-propanol.

6. A compound of claim 1 wherein said compound is 1-[(4-propenyl-2-methoxy)-phenoxy]-3-[(2-methoxyphenoxyethyl)amino]-propanol.

7. A compound of claim 1 wherein said compound is N-[4-(2-hydroxy-3-(4-oxyethylamino-3-methoxycinnamic acid)propoxy)-3-methoxy]-1-propylenyl-benzene.

8. A compound of claim 1 wherein said compound is N-[4-(2-hydroxy-3-(4-oxyethyl-amino-3-methoxybenzoic acid)propoxy)-3-methoxybenzyl]-nonanamide.

9. A compound of claim 1 wherein said compound is N-[4-(2-hydroxy-3-(4-oxyethyl-amino-3-methoxybenzoid acid)propoxy)-3-methoxy]-1-propenylbenzene.

10. A compound of claim 1 wherein said compound is N-[4-(2-hydroxy-3-(4-oxyethyl-amino-3-methoxycinnamic acid)propoxy)-3-methoxybenzyl]-nonanamide.

11. A compound of claim 1 wherein said compound is N-[4-(2-hydroxy-3-(1-oxyethyl-amino-4-oxyacetic acid benzene)propoxy)-3-methoxy]-1-propenylbenzene.

12. A compound of claim 1 wherein said compound is N-[4-(4-ethylamino-1-oxyacetic acid benzene ethoxy]-1-oxyacetic acid ethyl ester benzene.

* * * * *